United States Patent
Eagleman et al.

(10) Patent No.: US 8,343,066 B1
(45) Date of Patent: Jan. 1, 2013

(54) DEVICE AND METHOD FOR RAPID MEASUREMENT OF REPETITION SUPPRESSION IN THE BRAIN

(75) Inventors: David M. Eagleman, Houston, TX (US); Vani Pariyadath, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 886 days.

(21) Appl. No.: 12/240,782

(22) Filed: Sep. 29, 2008

Related U.S. Application Data

(60) Provisional application No. 60/975,650, filed on Sep. 27, 2007.

(51) Int. Cl.
*A61B 13/00* (2006.01)
(52) U.S. Cl. .................................................. 600/558
(58) Field of Classification Search .................. 600/558, 600/300
See application file for complete search history.

(56) References Cited

OTHER PUBLICATIONS

Black et al., "The flicker-fusion threshold in schizophrenia and depression," *New Zealand Medical Journal*, 81(535): 244-246, 1975.
Bowen et al., "Visual Persistence: Effects of Flash Luminance, Duration and Energy," *Vision Research*, 14:295-303, 1974.
Daskalakis et al., "Transcranial magnetic stimulation: A new investigational and treatment tool in psychiatry," *J. Neuropsychiatry Clin. Neurosci.*, 14(4): 406-415, 2002.
Gandhi et al., "Timing judgments in schizophrenia," Paper presented at Society for Neuroscience, 2007.
Grill-Spector et al., "Repetition and the brain: neural models of stimulus-specific effects," *Trends in Cognitive Sciences*, 10(1): 14-23, 2006.
Kanai and Watanabe, "Visual onset expands subjective time," *Percept Psychophys*, 68(7): 1113-1123, 2006.
Kiehl and Liddle, "An event-related functional magnetic resonance imaging study of an auditory oddball task in schizophrenia," *Schizophrenia Research*, 48: 159-171, 2001.
Morrone et al, "Saccadic eye movements cause compression of time as well as space," *Nat. Neurosci.*, 8(7): 950-954, 2005.
Rose and Summers, "Duration illusions in a train of visual stimuli," *Perception*, 24(1): 1177-1187, 2005.
Saucer and Sweetbaum, "Perception of the shortest noticeable dark time by schizophrenics," *Science*, 127(3300): 698-699, 1958.
Slaghuis and Bishop, "Luminance flicker sensitivity in positive- and negative-symptom schizophrenia," *Exp. Brain Res.*, 138:88-99, 2001.
Ulrich et al, "Perceived duration of expected and unexpected stimuli," *Psychological Research*, 70:77-87, 2006.
Yarrow et al., "Illusory perceptions of space and time preserve cross-saccadic perceptual continuity," *Nature*, 414(6861): 302-305, 2001.
Pariyadath and Eagleman, "The Proliferation Effect: a new psychophysical paradigm based on novelty and its effect on subjective duration," Poster 303.18/XX23, presented at Society for Neuroscience, 2007.

*Primary Examiner* — Brian Szmal
(74) *Attorney, Agent, or Firm* — Fulbright & Jaworski L.L.P.

(57) ABSTRACT

Neural responses to a repeated stimulus typically diminish, an effect known as repetition suppression. When a single visual stimulus (e.g., letter of the alphabet, word, object, face) is serially flashed in different locations of a display, several stimuli appear to be present simultaneously due to an effect known as persistence of vision. Normal human observers' estimates of how many stimuli they perceived at any instant of time are significantly lower when the same stimulus is flashed repeatedly than when a different stimulus is used for each flash. This is a result of the brain's diminishing response (repetition suppression) to the repeated stimuli. The present invention generally relates to methods for assessing the normality of neural performance, particularly as relates to the integrity of cortical inhibition, visual persistence, proliferation effect, and repetition suppression. Deficits in repetition suppression serve as early and confirmatory measures of cognitive disorders such as schizophrenia.

5 Claims, 5 Drawing Sheets

DEVICE AND METHOD FOR RAPID MEASUREMENT OF REPETITION SUPPRESSION IN THE BRAIN

CROSS-REFERENCE TO RELATED APPLICATIONS

This Application claims under 35 U.S.C. 119(e) the benefit of U.S. Provisional Application 60/975,650 filed on Sep. 27, 2007, the content of which is incorporated herein in its entirety.

STATEMENT REGARDING FEDERALLY SPONSORED RESEARCH OR DEVELOPMENT

The present invention was developed at least in part with funds from National Institutes of Health RO1 Grant NS053960. The United States Government has certain rights in the invention.

TECHNICAL FIELD

The present invention generally relates to devices and methods for assessing the normality of neural performance, particularly as relates to the integrity of cortical inhibition, visual persistence, proliferation effect, and repetition suppression. Deficits in repetition suppression serve as early and confirmatory measures of cognitive disorders such as schizophrenia.

BACKGROUND OF THE INVENTION

How the brain represents duration remains an unsolved problem (Eagleman et al., 2005). It is clear that physical time does not have a direct mapping onto perceived time—instead, subjective duration judgments are surprisingly prone to distortions (Eagleman, 2008; Kanai et al, 2006; Morrone et al., 2005; Nakajima et al., 1992; Yarrow et al., 2001), such that two stimuli of identical duration can be perceived to last different amounts of time. For example, observers watching a repeated stimulus erroneously report that the first presentation (Kanai and Watanabe, 2006; Pariyadath and Eagleman, 2007; Rose and Summers, 1995) and any 'oddball' presentation (Pariyadath and Eagleman, 2007; Tse et al., 2004; Ulrich et al., 2006) appear longer in duration than the other presentations.

Although these duration illusions were originally suggested to be caused by increases in attention (Rose and Summers, 1995; Tse et al., 2004), it has been previously shown that the emotional salience of an oddball presentation has no effect on the illusion (Pariyadath and Eagleman, 2007), suggesting that the effect has more to do with the stimulus predictability than the amount of attentional deployment.

In flicker fusion experiments, a light is rapidly turned on and off: at a low frequency, flicker is perceived, while at a high frequency, the light appears to be steady. The frequency at which perception switches from flicker to a steady light is called the critical flicker fusion threshold (CFFT). CFFT experiments always consist of a single stimulus (the light) presented repeatedly. There are subjective duration differences when viewing familiar versus novel stimuli, thus, the inventors discovered that the CFFT would change if the rapid stimulus was made novel each time it appeared.

The perceived duration of novel and repeated stimuli map on to measured neural responses to the same (Grill-Spector et al., 2006). Normal human brains show diminishing responses to stimuli that are repeated over and over. This effect is known as repetition suppression (RS). In humans, these differential responses to familiar and novel stimuli are seen using electroencephalography (Grill-Spector et al., 2006), functional magnetic resonance imaging (Henson and Rugg, 2001), positron emission tomography (Buckner et al., 1995) and magnetoencephalography (Ishai et al., 2006). In non-human primates, the same phenomenon is observed by measuring the firing rates of individual neurons in higher cortical areas (Tahy et al., 1993; Rainer and Miller, 2000).

In some disorders, such as schizophrenia, RS is impaired, as evidenced by an impaired pre-pulse inhibition of the startle response (Hong et al., 2007), impaired mismatch negativity (Light and Braff, 2005), and abnormal processing of oddball stimuli (Kiehl and Liddle, 2001). Schizophrenic patients also have a lower sensitivity for detecting flicker (Black et al., 1975; Slaghuis and Bishop, 2001), which indicates that repeatedly flashed stimuli, which diminish in perceived duration in a normal brain, seem to last longer to a schizophrenic brain (Pariyadath and Eagleman, 2007). Collectively, these findings paint a picture of reduced or absent RS in schizophrenic patients. That is, to a schizophrenic brain, certain types of repeated stimuli will continue to appear novel. Presumably this reflects a deficit in cortical inhibition, which normally functions to provide RS (Daskalakis et al., 2002a; Daskalakis et al., 2002b). Further, data indicate that damage to the brain compromises performance on simple timing tasks. Therefore, measures of time perception, which are currently missing from the clinical landscape, are well-suited to provide a rapid and inexpensive way to screen for and rapidly identify traumatic brain injury (TBI). Currently used measures to highlight subtle brain damage (such as memory or cognition batteries) take a good deal of time and expertise to administer, rendering them ineffectual on the field. By contrast, simple timing tasks have the potential to highlight damage quickly and with no human administrator.

The measure of repetition suppression and visual persistence is a powerful diagnostic tool which can be used in the study of cognitive disorders. However, despite the increased knowledge that has been gained in recent years about the factors influencing repetition suppression, the basic measuring methodology has remained essentially unchanged. There is currently no method other than that disclosed here that allows inexpensive and rapid measurement of repetition suppression. Instead, all currently available methods use the technologies referred to in the studies above, namely, electroencephalography (Grill-Spector et al., 2006), functional magnetic resonance imaging (Henson and Rugg, 2001), positron emission tomography (Buckner et al., 1995) and magnetoencephalography (Ishai et al., 2006). These methods are uniformly expensive, time intensive, cause physical discomfort, necessitate training and expertise in administering the test, and require substantial data analysis. Therefore, there would be substantial interest in computer software or a physical device that could instantly and inexpensively yield an accurate measure of visual persistence and/or repetition suppression in human observers.

BRIEF SUMMARY OF THE INVENTION

An embodiment of the invention is a method of assessing visual persistence in an individual, comprising: displaying a sequence of stimuli on a visual display to an individual wherein each stimulus is displayed for a time period less than a predetermined perception limit, and ascertaining the number of displayed stimuli simultaneously perceived by the individual. In a specific embodiment of the invention, no sequential stimuli are displayed at substantially overlapping time periods.

Another embodiment of the invention is a method of assessing the risk an individual has a cognitive disorder, comprising: displaying a sequence of stimuli on a visual display to an individual wherein each stimulus is displayed for a time period less than a predetermined perception limit; ascertaining the number of displayed stimuli perceived by the individual; and comparing the number of displayed stimuli simultaneously perceived by the individual to a predetermined number. In a specific embodiment of the invention, no sequential stimuli are displayed at substantially overlapping time periods.

Another embodiment of the invention is a computer program product for measuring visual persistence, the computer program product comprising: a computer usable medium having computer usable program code embodied therewith, the computer usable program code comprising: computer usable program code configured to instruct a device to carry out the steps of: displaying a sequence of stimuli on a visual display wherein each stimulus is displayed for a time period less than a predetermined perception limit; and computer usable program code configured to instruct a device to record a user inputted number. In a further embodiment of the invention, no sequential stimuli are displayed at substantially overlapping time periods.

An embodiment of the invention is a method of assessing visual persistence in an individual, comprising: a step for displaying a sequence of stimuli on a visual display to an individual, wherein each stimulus is displayed for a time period less than a predetermined perception limit, and wherein no sequential stimulus are displayed at substantially overlapping time periods, and a step for ascertaining the number of displayed stimuli simultaneously perceived by the individual.

Another embodiment of the invention is a method of measuring repetition suppression in an individual comprising: a step for measuring visual persistence of a series of substantially identical stimuli in an individual; a step for measuring visual persistence of a random sequence in the individual; a step for calculating the difference in random and repeated sequences in the individual, wherein the difference represents the repetition suppression in the individual. A further embodiment of the invention additionally comprises a step for comparing the repetition suppression in the individual to a normal range of repetition suppression, wherein a deviation from the normal range indicates a cognitive disorder. In a specific embodiment of the invention, the cognitive disorder is autism or schizophrenia.

Another specific embodiment of the invention is a method of assessing visual persistence in an individual, comprising the sequential steps of: 1) providing a display to an individual; 2) presenting a first image on the display; 3) removing the image from the display; 4) presenting a subsequent image on the display at a location different from the previous image; wherein steps 3 and 4 are repeated a set number of times; and 5) ascertaining the number of displayed images simultaneously perceived by the individual.

In a particular embodiment of the invention, each sequential stimulus is displayed in a location different from the previously displayed stimulus. In another embodiment, each sequential stimulus is displayed in a different quadrant of the display. In a further embodiment, the stimuli are from the group consisting of pictures, words, non-words, characters, and any combination thereof. In another embodiment, each stimulus is the same. In another embodiment, each stimulus is different. In further embodiment, each stimulus is displayed for substantially equal amounts of time. In another embodiment, a time gap occurs between at least one sequential pair of stimuli. In another embodiment, at least two stimuli are displayed within a time period less than the predetermined perception limit. In another embodiment, at least two stimuli are displayed within 100 ms of each other. In another embodiment, each stimulus is displayed at about equal intervals. In another embodiment, the sequence of stimuli comprises at least 2 stimuli, at least 3 stimuli, at least 4 stimuli, at least 5 stimuli, at least 10 stimuli, at least 25 stimuli, at least 35 stimuli, at least 50 stimuli, at least 60 stimuli, at least 65 stimuli, at least 75 stimuli, at least 100 stimuli, greater than 100 stimuli, greater than 500 stimuli, or greater than 1000 stimuli. In a further embodiment, the time period each stimulus is displayed is greater than 0.1 ms, is greater than 1 ms, is greater than 2 ms, is greater than 5 ms, is greater than 10 ms, is greater than 20 ms, is greater than 30 ms, is greater than 40 ms, is greater than 50 ms, is greater than 60 ms, is greater than 70 ms, or is greater than 80 ms. In embodiments of the invention, the sequence of stimuli is displayed at a constant rate between 5 and 500 Hz. In specific embodiments, the sequence of stimuli are displayed at 500, 400, 300, 200, 100, 75, 50, 25, 17, 12, 10, 9, 8, 7, 6, or 5 Hz. In another embodiment, the sequence of stimuli takes less than 1 second to display, takes less than 2 seconds to display, takes less than 3 seconds to display, or takes less than 5 seconds to display. In embodiments of the invention, the predetermined perception limit is a range that falls between 10 and 180 ms. In another specific embodiment, the predetermined perception limit is about 10, is about 20, is about 30, is about 40, is about 50, is about 60, is about 70 ms, is about 80 ms, is about 90 ms, is about 100 ms, is about 110 ms, is about 120 ms, is about 130 ms, is about 140 ms, is about 150 ms, is about 160 ms, is about 170 ms, or is about 180 ms.

In a specific embodiment of the invention, multiple repetitions of the sequence display followed by input is performed. In another embodiment, the number of perceived stimuli are averaged over all repetitions. In a further embodiment, repeated sequence results are compared to random sequence results. In specific embodiment, the difference or ratio between repeated sequence visual persistence and random sequence visual persistence is the repetition suppression. In another embodiment, repetition suppression may indicate a cognitive impairment or cognitive disorder. In a specific embodiment, the cognitive impairment is due to drug use. In another specific embodiment, the cognitive disorder is autism or schizophrenia.

In one embodiment of the invention, the method further comprises assessing a cognitive disorder or cognitive impairment by comparing the number of perceived stimuli with a predetermined number. In another embodiment, repetition suppression may indicate a cognitive impairment or cognitive disorder. In a specific embodiment, the cognitive impairment is due to drug use. In another specific embodiment, the cognitive disorder is autism or schizophrenia. In another embodiment, the predetermined number is a range of normal repetition suppression given by a health population. In a specific embodiment, the difference between repetition suppression of the method and the predetermined number indicates the risk an individual has a cognitive disorder or impairment.

In a specific embodiment each stimulus is different and the predetermined number is the number of displayed stimuli perceived by the individual when all stimuli are the same. In another embodiment the difference between or ratio of the repeated and random stimuli perception number indicates the risk of the individual for a cognitive disorder or cognitive impairment.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to characterize the invention, both as to its organization and method of operation, together with further objects and advantages will be better understood from the following description when considered in the context of the accompanying figures. It is to be expressly understood, however, that each of the figures is provided for the purpose of illustration and description only and is not intended as a definition of the limits of the present invention.

BRIEF DESCRIPTION OF THE DRAWINGS

FIG. 1A shows example sequences of stimulus presentation and perceived numerosity for repeated and random stimuli. FIG. 1B shows the number of characters perceived to be present for repeated and random stimuli. Participants report more characters present on screen when the stimuli are different than when they are repeated. n=31. Error bars S.E.M. FIG. 1C is an example of the visual persistence of a repeated stimulus that is contracted compared to novel stimulus. Even while participants are not asked to make an explicit temporal judgment, the duration distortion nonetheless changes their interpretation of the visual scene. FIG. 1D demonstrates that the duty cycle does not change numerosity estimates. Stimuli were presented for different physical durations while keeping the presentation frequency constant. No significant difference was found in perceived numerosity for different stimulus durations when maintaining a constant stimulus presentation frequency (** indicates $p<0.01$; * indicates $p<0.05$, paired t-tests). n=31. Error bars S.E.M.

FIG. 2A shows that participants report more objects were simultaneously present on screen when the objects were different (random) as compared to repeated (n=16). FIG. 2B shows that more faces were reported to be simultaneously present when the faces were different as compared to repeated. (n=15). * indicates $p<0.05$, paired t-test. Error bars S.E.M. Conditions were identical to the first experiment (FIG. 1).

FIG. 4A bar 1 are healthy controls that report differential numerosity on the proliferation task using repeated and random words ($p=0.01$, paired t-test, n=15), with a repeat-to-random ratio of 0.859 (first bar). In contrast, schizophrenic patients who are unmedicated or within the first 3 days of medication have repeat-to-random ratios of >1.0 ($2^{nd}$ and $3^{rd}$ bar). By day 8 of the medication schedule, their ratios have normalized ($4^{th}$ bar). FIG. 4B is a schematic of panel A: Viewing flashed words, participants report numerosity in repeat and random conditions. Because schizophrenic patients have deficient repetition suppression, their brains do not distinguish repeated and random conditions.

DETAILED DESCRIPTION OF THE INVENTION

Figure 1:
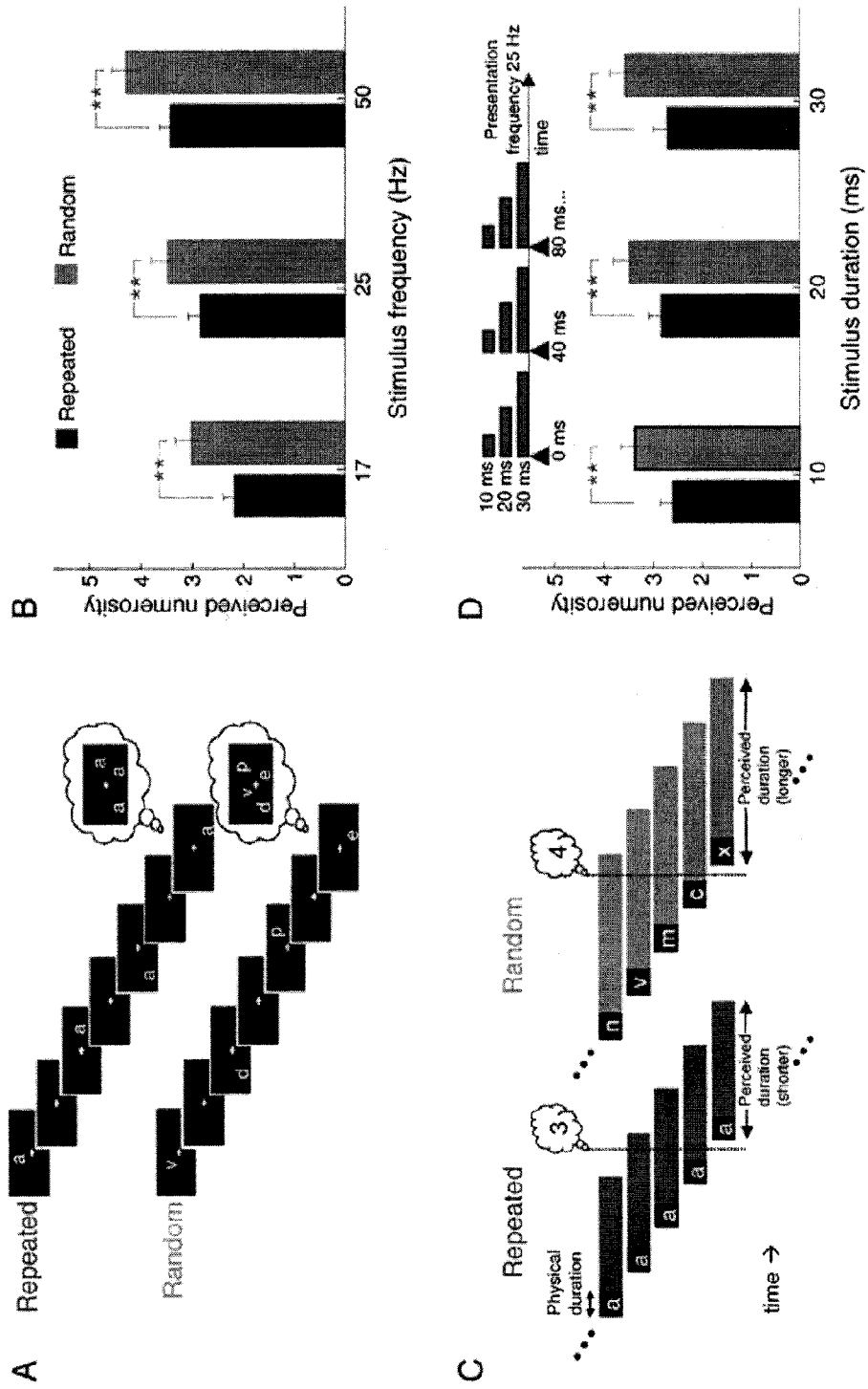
FIG. 1 demonstrates that repeated stimuli subjectively proliferate less than random stimuli.

In accordance with certain embodiments of the invention, an instant, inexpensive, automated method is provided for measuring repetition suppression and/or visual persistence.

In one embodiment of the invention, observers sit in front of a computer monitor and fixate a cross at the center of the screen. On each trial, characters of the alphabet are flashed one at a time in a randomized location within 6.6° of fixation. In 72 randomly interleaved trials, stimulus durations are 10, 20 or 30 ms (fixed within a trial), and the inter-stimulus interval were always equal to the stimulus duration; this yields presentation rates of 50, 25 and 17 Hz. To ensure that characters are not presented in close proximity on successive frames, each character is presented in a different quadrant from the previous presentation. Any type of display may be considered for use. Displays such as cathode-ray-tube monitors, plasma screens, a liquid crystal display, groups of light emitting diode arrays, or any other visual display may be used in the invention. In another embodiment, diagnostic efficacy is determined by cross-correlating with physician diagnosis.

Perceptually, this rapidly presented stimulus does not map onto the physical reality because of visual persistence, the phenomenon that a briefly presented stimulus appears to last longer than the time it was physically presented: in general, stimuli <100 ms in physical duration seem to last for ~100 ms (Lollo, 1977; Bown et al., 1974; Efron, 1970). Beyond this threshold, stimuli are perceived approximately accurately, i.e., close to their true physical duration. Because of visual persistence, each stimulus in the presentation seems to last longer than presented, and therefore the physically-present stimulus is accompanied by the 'ghosts' of stimuli that were presented recently. Thus more than one character appears to temporally overlap on screen. We refer to the resulting multiplicity of stimuli as the proliferation effect (Pariyadath and Eagleman, submitted).

In one embodiment of the invention, two conditions are employed: in the first, the same character is presented; in the second, different characters are presented. Trials may last 1320 msec and may end with a mask of white noise. Participants then use a number pad to report the number of characters subjectively present on screen at any one moment of time, that is, how many characters appear to share screen time. Other input methods are also considered for the invention, such as touch screen displays. One of skill in the art will know a variety of methods that can ascertain the number of stimuli the participant perceives.

Participants' estimates of how many characters they perceive on screen simultaneously vary between the repeated and random conditions which in one embodiment of the invention is used to determine repetition suppression. In one embodiment this effect occurs because repetition contracts the duration of visual persistence, thus explaining the differential reports for perceived numerosity for repeated and novel stimuli: a contraction in the visual persistence of repeated stimuli leads to less temporal overlap and a reduced number of stimuli perceived to be simultaneously present.

The differential proliferation effect for repeated and random stimuli is not restricted to characters, but instead has many possible embodiments. For example, when observers are presented with variations of the above display in which the stimuli consist of photographs of everyday objects or faces, the same effect is found to occur. That is, in the 'repeated' conditions, the same image is serially presented; in the 'random' conditions, different images are randomly selected. As in the first experiment, observers perceive fewer stimuli on screen when the stimulus is presented repeatedly as compared with random stimuli. Therefore, repetition related duration distortions generalize beyond letters, consistent with the wide-ranging stimuli that lead to repetition suppression. Non-limiting display types of stimuli include examples such as characters, images, faces, pictures, figures, drawings, symbols.

In one embodiment of the invention, the 'repeated' stimulus has to only be predictable (not necessarily repeated) in order to reduce its numerosity. Thus, in another embodiment, letters of the alphabet are serially flashed in sequence, and in a second condition, letters of the alphabet are serially flashed in scrambled order.

The findings of the effects of repetition on subjective duration have led to an embodiment of the present disclosure: a novel method to rapidly and non-invasively appraise deficits of repetition suppression in human subjects, as found, for example, in schizophrenia.

Figure 4:
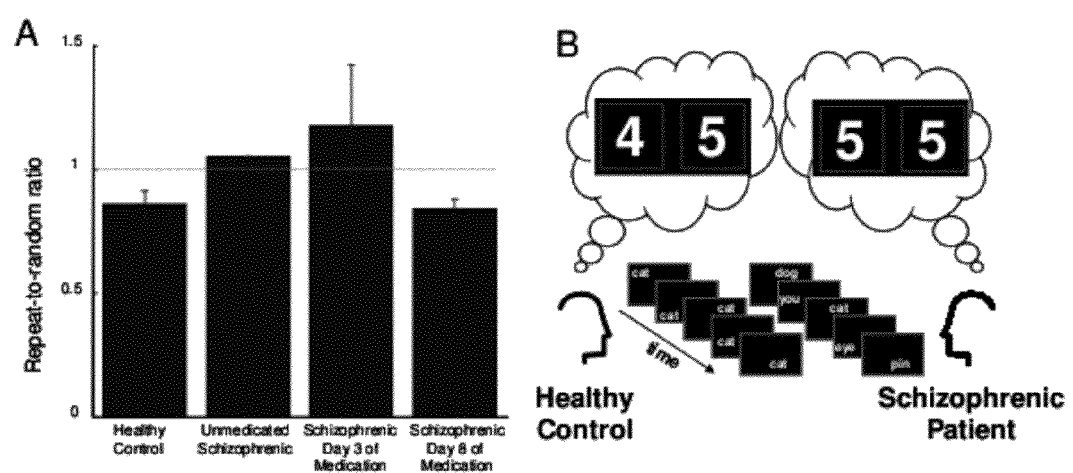
FIG. 4 demonstrates an exemplary non-invasive diagnostic tool for impaired repetition suppression.

In one embodiment, the proliferation effect is leveraged as an instant diagnostic tool. For example, schizophrenic patients show particularly deficient repetition suppression for stimuli such as pseudo-words (Guillem et al., 2001). It is found that healthy controls show a clear difference in their proliferation effect using actual words (FIG. 4A). Schizophrenic patients fail to perceive this differential numerosity (FIG. 4B), and could thereby be referred for further examination. In one embodiment, this non-invasive, rapid method serves as a screening tool for early diagnosis.

This use would not be exclusive to schizophrenia, since other scenarios can also produce deficits in repetition suppression. For example, benzodiazepines reduce novelty response (Thiel et al., 2001); thus, participants treated with benzodiazepines may be expected to report no differential numerosity between random and repeated stimuli. The benzodiazepine case, however, could be still potentially distinguished from schizophrenia by the magnitudes of the numerosities, which would be expected to be lower (e.g., reporting '4' and '4' for the stimuli in FIG. 4B). Further, autistic patients show deficits in repetition suppression (Dawson et al., 2005). In one embodiment of the invention a different palette of stimuli (for example, familiar faces instead of words) allows a discrimination of the different clinical conditions.

Other objects, features and advantages of the present invention will become apparent from the detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DEFINITIONS

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

As used herein, an "individual" is an appropriate subject for the method of the present invention. Individuals may also be referred to as "participant," "patients" or "subjects."

As used herein, "substantially overlapping time periods" means a period that will have a substantial effect on an individuals perception. For example, the phrase "no sequential stimulus are displayed at substantially overlapping time periods" means that no sequential stimulus are displayed at overlapping time periods that would effect the outcome of the experiment. In this example, the time period would be less than about 50 ms, less than about 40 ms, less than about 30 ms, less than about 20 ms, less than about 10 ms, less than about 1 ms, or less than about 0.1 ms.

The phrase "sequence of stimuli," as used herein, refers to a group of individual stimulus that are displayed sequentially. Each stimulus may occur at overlapping time periods with a previous or sequential stimulus or may occur individually with no other stimuli displayed. There may be a time period between each displayed stimulus in which no stimulus occurs. In one embodiment of the invention, no two stimulus occur at the same time. In a further embodiment of the invention, each stimulus is displayed for about the same time period as every other stimulus. It is understood that to form a "sequence," the stimuli do not occur simultaneously. In one embodiment, a stimulus is displayed every 5 ms, 10 ms, 20 ms, 30 ms, 40 ms, 50 ms, 60 ms, 70 ms, 80 ms, or 90 ms.

The term "visual display" means any display on which the sequence of stimuli can be displayed to an individual. This includes at least displays such as cathode-ray-tube monitors, plasma screens, a liquid crystal display, groups of light emitting diode array.

As used herein, "perception limit" refers to the minimum amount of time at which an individual's perception of the time period a stimulus is displayed equals the actual time period a stimulus is displayed. A rough average of the perception limit is around 100 ms, however, one of skill in the art knows how to optimize this perception limit based on an individual or a population of individuals. For instance, the perception limit of an older population may be greater than that of a younger population. Exemplary perception limits are 180 ms, 170 ms, 160 ms 150 ms, 140 ms, 130 ms, 120 ms, 110 ms, 100 ms, 90 ms, 80 ms, 70 ms, 60 ms, 50 ms or anywhere in between. The perception limit may also represent a range of perception over a population. Exemplary ranges for the perception limit are 30 to 150 ms, 40 to 140 ms, 50 to 130 ms, 60 to 120 ms, 70 to 110 ms, 80 to 100 ms.

The term "character" refers to an individual letter, number, line or other symbol.

The term "word" refers to a collection of individual letters, numbers or symbols that is recognizable to the individual to whom the word is being displayed as a word. The word is a written or printed character or combination of characters representing a spoken word.

The term "non-words" refers to two or more characters positioned in a continuous row, where the characters form word-like structures, but the word-like structure is not a familiar word to the individual viewing the non-word. Non-limiting examples of non-words using the English language alphabet are dk, vdasdf, erbbv, eifpoi, afsd-sfa.

Figure 5:
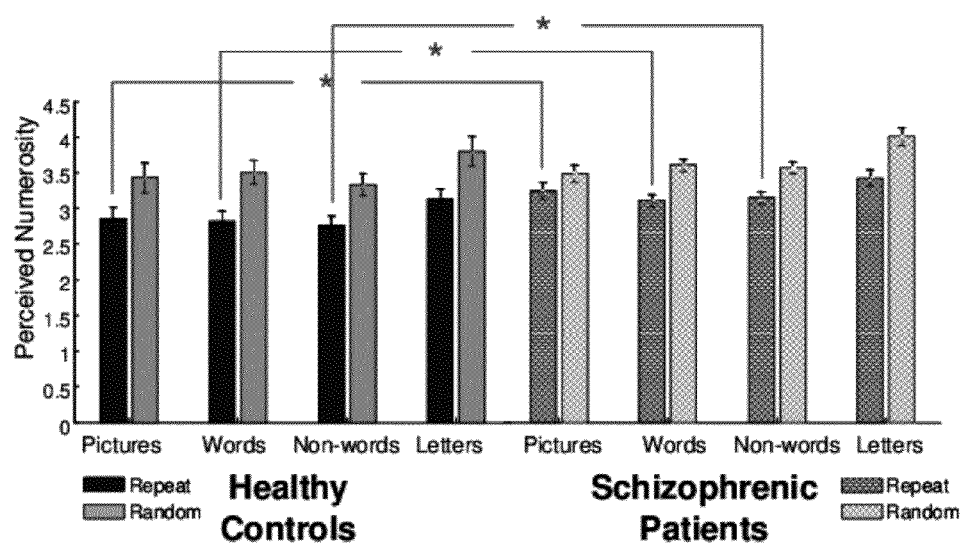
FIG. 5 shows that schizophrenic patients perceive similar numerosity for random stimuli compared to healthy controls but perceive more stimuli on screen when the stimulus is repeated. * indicates $p<0.05$, one tailed t-test.

The term "normal range" refers to a range that represents a "normal" individual or population of "normal" individuals. The normal range is a range of values a healthy control population would give. In the context of schizophrenia, "normal" refers to a population of individuals that do not have schizophrenia. For example, a normal range of repetition suppression for non-schizophrenic individuals is given in FIG. 5. Given this invention disclosure, one of skill in the art would know how to calculate a normal repetition suppression range. The normal range may also be optimized for a certain population of normal individuals. This could be calculated from historical data, and may be a ratio or difference. In one embodiment, the normal range of values is also a population matched to the tested population; e.g., if the tested population was between the ages of 20 and 30, the normal range would be taken from a healthy control population between the ages of 20 and 30.

The terms "visual persistence," refers to the phenomenon that a briefly presented stimulus appears to last longer than the time it was physically presented: in general, stimuli <100 ms in physical duration seem to last for ~100 ms (Bowen et al., 1974; Di Lollo, 1977; Efron, 1970). Beyond this threshold, stimuli are perceived approximately accurately, i.e., close to their true physical duration. Because of visual persistence, the physically-present stimulus is accompanied by the 'ghosts' of stimuli that were presented recently. Thus more than one character appears to temporally overlap on screen. The perceived multiplicity of stimuli is the proliferation effect.

As used herein "repetition suppression," refers to the effect of sequentially observing two identical stimuli of identical duration, and perceiving that the secondly presented stimulus occur in a shorter time period that the first stimulus i.e., when stimulus are identical, perception of the time a recurring identical stimulus is displayed is shorter. When the recurring stimulus are random, no time perception change occurs. Thus, the visual persistence of repetitively displayed stimuli are suppressed. Repetition suppression may be affected by autism, schizophrenia, drug use, or benzodiazepines, for example.

The term "cognitive disorder," as used herein, refers to any disorder which effects visual persistence or repetition suppression. For example, autistic or schizophrenic patients show deficits in repetition suppression.

The term "cognitive impairment," as used herein, refers to any impairment in visual persistence or repetition suppression. Cognitive impairment may be caused by autism, schizophrenia, drug use, or benzodiazepines, for example.

The terms "stimulus" or "stimuli," as used herein, refer to a specific visual change in a display. For example, the stimulus could be the display of a letter on a blank screen. Non-limiting examples of stimulus are letters, numbers, symbols, words, pictures, images, faces, or figures. Removal of the stimulus is equated to removal of the specific visual change from the display to result in the previous unaltered state of the display. In one embodiment, the display without stimulus consists of only one color or no color, i.e., a black screen or a white screen.

The term "time gap," as used herein, refers to a period of time between displays of stimulus in which no stimulus is displayed. In an embodiment of the invention, the time gap is between 1 and 100 ms. In a specific embodiment, the time gap is 1 ms, 5 ms, 10 ms, 20 ms, 30 ms, 40 ms, 50 ms, 60 ms, 70 ms, 80 ms, or 90 ms.

The phrase "repeated stimuli," refers to a sequence of stimuli in which the form of each stimulus is substantially identical to the previous stimuli. For example, the sequence of repeated stimuli could be the letter "L" repeated. An example of repeated stimuli is shown in FIG. 1A.

The phrase "random stimuli," refers to sequence of stimuli in which the form of each stimulus is substantially non-identical to the previous stimuli. For example, the sequence of repeated stimuli could be the letter "L" followed by the letter "K" followed by the letter "X". An example of random stimuli is shown in FIG. 1A.

As used herein, the phrase "predetermined number" refers to a number that is calculated prior to the experiment. For instance, the predetermined number could be calculated from a population of normal individuals. An example of a predetermined number used to assess a cognitive disorder is given in FIG. 4A, where a healthy control population is compared to an unmediated and medicated schizophrenic population, and a number over about 0.9 or 1 indicates schizophrenia. This predetermined number will vary depending on the frequency at which the stimuli are presented, on the control population type, and on the type of cognitive disorder being assessed, for example. One of skill in the art, given this disclosure, would know how to calculate each specific predetermined number.

Schizophrenia

Schizophrenia is a severe cognitive disorder involving chronic or recurrent psychosis. Psychosis is a break with reality which is usually observed as a combination of delusions, hallucinations, and chaotic behavior. Although psychosis is a main symptom of schizophrenia, other psychiatric and medical disorders may also account for psychosis. The absence of quantitative pathognomonic features, or of laboratory or neuropsychological tests, makes diagnosing schizophrenia difficult.

The heterogeneous presentation of schizophrenia relates to the existence of four largely independent symptom clusters, identified by factor analysis of observed symptoms in large groups of schizophrenia patients (Lindenmayer et al., 1994). The fundamental domains of the disorder are: positive symptoms, negative symptoms, cognitive impairments, and affective disturbance. Schizophrenia has traditionally been divided into several diagnostic subtypes: paranoid, disorganized, catatonic, residual, undifferentiated, schizophreniform disorder, and Schizoaffective disorder.

Positive symptoms are the presentations of psychosis. "Positive" refers to the individual having these symptoms, when a "normal" individual would not. Delusions are the most common psychotic symptom in schizophrenia, occurring in 65 percent of patients (Breier and Berg, 1999; Appelbaum et al., 1999). Hallucinations and thought disorganization each are seen in about 50 percent of patients. Auditory hallucinations are the most common sensory disturbance in schizophrenia, but visual, tactile, olfactory, and gustatory hallucinations also occur (Szymanski et al, 1996). Most patients experience a combination of delusions, hallucinations, and disorganization (Appelbaum et al., 1999).

Negative symptoms represent the diminution or absence of characteristics a "normal" individual would possess. Schizophrenic individuals may experience a loss of affective responsiveness, verbal expression, personal motivation, enjoyment, social drive, motivation, and/or attention to the environment (Andreasen, 1982). All aspects of cognitive function are affected by schizophrenia, including attention, language, memory, and executive function (Saykin et al., 1991). In most cases, significant deficits are present from birth, followed by additional moderate decline with the onset of the active illness (Russell et al., 1997; Russell et al, 1997; Seidman et al., 2006; Woodberry et al., 2008).

Affective disturbance are problems with mood and affect. Inappropriate, bizarre, or unmodulated affect may be observed. The combination of blunted, inappropriate, and odd expression is commonly seen in schizophrenia (Edwards et al., 2002). Mood disturbance and depression is also seen.

Cognitive impairments include working memory defects, attentional dysfunction, verbal and visual learning and memory, processing speed, and social learning (Gruzelier et al., 1988; Goldberg et al., 1990; Braff et al., 1991; Gur et al., 1991; Liddle and Morris, 1991; Gold et al., 1992). No cognitive domains are entirely spared, and deficits in performance are highly correlated within persons. However, schizophrenic subjects in many of the studies show a pattern of deficits, ruling out a lack of motivation as a factor in performance.

There are no laboratory or clinical studies for diagnosis. The diagnosis is made on the basis of a pattern of psychotic symptoms and functional deterioration, in the absence of other explanations. A complete review of schizophrenia, including symptoms and treatment can be found in Diagnostic and Statistical Manual of Mental Disorder, $4^{th}$ ed. American Psychiatric Association, Washington, D.C. 1994, (DSM) which is which is incorporated herein in its entirety. Additional information on other disorders which affect visual persistence and repetition suppression such as autism may also be found in the DSM.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The following first two examples are two possible embodiments of the testing method, neither of which require setup or calibration, and both of which yield a rapid assessment of repetition suppression in about 60 seconds or less.

Example 1

Exemplary Materials and Methods for Example 2

Participants consisted of graduate students and staff between the age of 18 and 45 at the Texas Medical Center with normal or corrected-to-normal vision; all were compensated for taking part in the experiments. Participants sat 59 cm from a CRT computer monitor (refresh rate 100 Hz) and fixated a cross at the center of the screen.

On each trial, stimuli were flashed one at a time in a randomized location within 6.6° of fixation. In 72 randomly interleaved trials, stimulus durations were 10, 20 or 30 ms (fixed within a trial), and the inter-stimulus interval was always equal to the stimulus duration; this yielded presentation rates of 50, 25 and 17 Hz. To ensure that stimuli were not presented in close proximity on successive frames, each stimulus was presented in a different quadrant from the previous presentation.

Trials lasted 1320 msec and ended with a mask of white noise. Participants then used a numberpad to report the number of stimuli perceived to have been present on screen at any one moment of time.

Letters (FIG. 1) were presented at 18.9 cd/m² in 128-point font size within 6.6° of fixation on black background. Photographs (FIG. 2) each spanned a visual angle of 0.02°. Stimuli were generated using Matlab and the psychophysical toolbox.

Example 2

The Proliferation Effect Differs for Novel and Repeated Stimuli

As described above, stimuli were rapidly flashed one-at-a-time in different positions on the screen. Perceptually, there appear to be several stimuli simultaneously present because of visual persistence. Two conditions were employed: in the first, the same character was presented ('Repeated'); in the second, different characters were presented ('Random', FIG. 1A). Participants reported perceived numerosity, i.e., how many characters appeared to be present on screen at any instant.

Participants' estimates of how many characters they perceived simultaneously on screen differed significantly between the repeated and random conditions (FIG. 1B). At a 50 Hz presentation rate, for example, observers reported an average of 3.4 characters on screen in the 'repeat' condition and 4.2 in the 'random' condition ($p<10^{-5}$, paired t-test; average within-subject standard deviation 0.91 [repeated] and 1.00 [random]). The different numerosities are summarized in the two conditions by calculating a repeat-to-random ratio, which in this case was 0.81. The difference between the two conditions holds across different stimulus frequencies, even while the absolute numerosity declines with lower frequencies. In one embodiment, these results indicate that repetition contracts the duration of visual persistence, and therefore there is less temporal overlap and a reduced number of stimuli perceived to be simultaneously present (FIG. 1C).

To further address whether the proliferation effect is predicated on visual persistence, attention was turned to the fact that brief stimuli (<100 ms) will be perceptually expanded to ~100 ms, irrespective of their physical durations (e.g., a 10 ms stimulus and a 30 ms stimulus will appear to last the same duration). Thus, in the next experiment, the presentation frequency was fixed at 25 Hz but changed the stimulus duration to 10, 20 or 30 ms (FIG. 1D, inset). Changing the duty cycle in this way had no effect on numerosity (FIG. 1D), consistent with the effect results from visual persistence of the stimuli, which makes the 10, 20 and 30 ms presentations perceptually equivalent.

The values of visual persistence that could account for the reported numerosities were calculated next. Since there was no way of knowing whether participants chose their numerosities based on the average number of perceived stimuli, or instead on the maximum number of perceived stimuli, visual persistence using both methods were calculated. The resulting estimates of visual persistence range from 84-180 ms (average method) or 61-121 ms (maximum method) for repeated stimuli and 68-132 ms (average method) or 41-81 ms (maximum method) for repeated stimuli. A single value for the window of visual persistence does not account for the perceived numerosities at all 3 frequencies in FIG. 1B; however, the data translate into visual persistence values consistent with their typically reported range of visual persistence (Di Lollo, 1977). The variability suggests the possibility of additional mechanisms at play in the different presentation frequencies.

Figure 3:
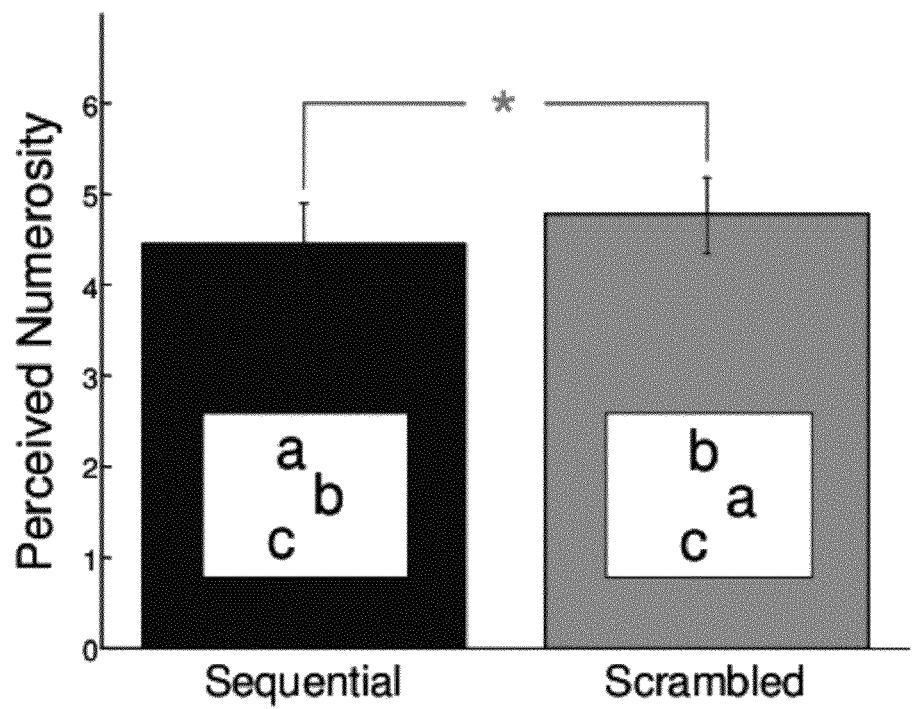
FIG. 3 shows that ordinal stimuli subjectively proliferate less when they are presented in sequence. Observers tend to report that more letters are present on screen when the letters are scrambled as compared with when they were sequential ($p<0.04$, paired t-test). Error bars S.E.M. n=14.

In one embodiment of the invention, the 'repeated' stimulus has to only be predictable (not necessarily repeated) in order to reduce its numerosity. Thus, in another embodiment, letters of the alphabet are serially flashed in sequence, and in a second condition, letters of the alphabet are serially flashed in scrambled order. Observers perceive more characters on screen simultaneously when characters are presented in random order as opposed to when they were presented in sequence (FIG. 3, sequential-to-scrambled ratio 0.93). In post-test interviews, observers fail to notice any difference between the two types of trials, indicating that conscious appreciation of ordinality and its violation does not play a role in this effect.

Example 2

The Repetition Effects Generalize to Pictures of Objects and Faces

Figure 2:
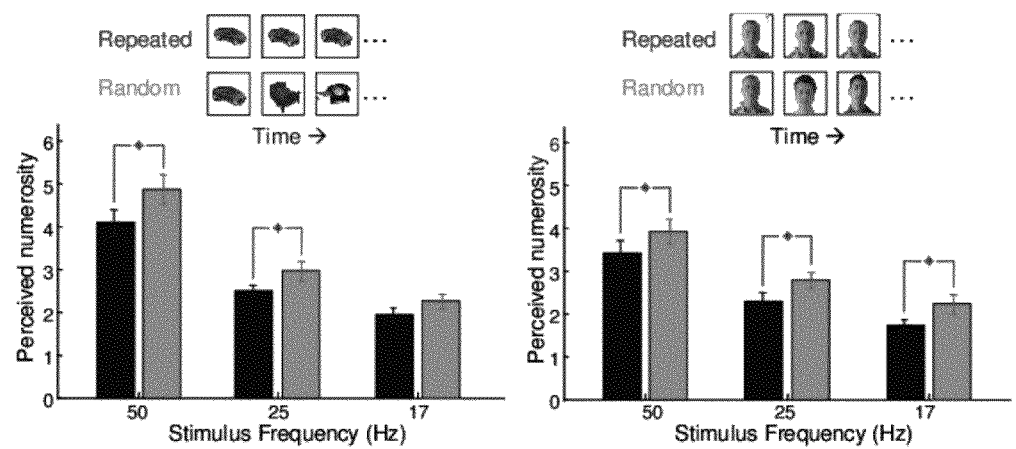
FIG. 2. shows decreased numerosity for repeated stimuli generalizes to objects and faces.

To determine whether the differential proliferation effect for repeated and random stimuli generalized beyond characters, participants were next presented with variations of the experiment in which the stimuli consisted of photographs of everyday objects (FIG. 2A) or faces (FIG. 2B). In the 'repeated' conditions, the same image was serially presented; in the 'random' conditions, different images were randomly selected (from a bank of 75 objects or 106 faces). Trial types were randomly interleaved. As in the first experiment, participants perceived fewer stimuli on screen when the stimulus was presented repeatedly as compared with random stimuli (FIG. 2) with an average repeat-to-random ratio of 0.88 in both cases. Therefore, repetition related duration distortions generalize beyond letters.

As a final control, the possibility that the perception of numerosity is sensitive to similarity or differences among stimulus elements was considered, and that the results may have nothing to do with duration. To test this, we presented 7 participants with brief static displays of same or different stimuli (analogous to the repeated and random conditions). Specifically, 3, 4 or 5 letters were presented simultaneously at random locations of the screen for three possible durations (10, 20 or 30 ms). With such static displays, participants perceived no difference in numerosity between the same and different conditions (p>0.66). Therefore, the results cannot be explained by differences in numerosity perception based on the low-level properties of the stimulus elements.

Example 3

Exemplary Discussion

The perceived durations of repeated stimuli are briefer than those of novel stimuli, even when participants are not asked to make explicit temporal judgments. These subjective durations have direct impact on the interpretation of the visual scene: participants perceive a different number of stimuli in repeated and random conditions. Without intending to limit the invention, these perceptual repercussions suggest that distorted durations are assigned on the fly instead of labeled retrospectively.

The possibility that the data in FIG. 1 might be explained by timing differences between normal apparent motion and transformational apparent motion (in which an object is perceived to change shape as it moves) was considered, but previous studies have found no difference in the strength of apparent motion when using same or different shapes (Burt and Sperling, 1981; Kolers and von Grunau, 1976; Navon, 1976), thus weighing against such an explanation. Moreover, attentional theories posit that an increased allocation of attentional resources results in increased perceived duration. These theories rest on the purported >120 ms required for allocating attention to a stimulus (see Tse, 2004); such an explanation is untenable for the present duration distortions.

In one embodiment, the perceived duration of a stimulus is dependent on the amplitude of the neural response it engenders (Eagleman, 2008; Pariyadath and Eagleman, 2007). In non-human primates, neuronal firing rates in higher cortical areas quickly diminish in response to repeated presentations of a stimulus (Fahy et al., 1993; Miller and Desimone, 1994), also known as repetition suppression. In humans, these differential responses to familiar and novel stimuli are seen using electroencephalography (Grill-Spector et al., 2006), functional magnetic resonance imaging (Grill-Spector et al., 2006; Henson and Rugg, 2001), positron emission tomography (Buckner et al., 1998) and magnetoencephalography (Ishai et al., 2006).

Without intending to limit the invention, these findings on the visual persistence of repeated stimuli provide an alternative explanation for previous findings. For example, the smallest interval required for two flashes to be perceived as separate is greater than the smallest interval needed between successive flashes in a train (Herrick, 1974). In other words, when measured in frequency, the two-flash flicker threshold is smaller than the critical flicker fusion threshold. Herrick appealed to probability summation to explain these results (Herrick, 1974); however, the simpler alternative is that when two flashes are presented one after the other, the visual persistence of the first causes it to overlap temporally with the second (provided that the ISI is less than 100 ms). But when a train of such flashes is presented, the visual persistence of the flashes contracts with repetition and one perceives the train as a series of events. The visual persistence of brief stimuli is contracted by repetition also offers a new framework for understanding 'change-related persistence': when a moving object undergoes a sudden change it is momentarily perceived as two separate objects (Moore et al., 2007), presumably because of the increased visual persistence of the novel presentation.

Without intending to limit the invention, the increased numerosity with random stimuli may also account for another observation: random dot kinematograms with lower coherence appear to have higher dot density (A. Tolias, personal communication). Conditions of high coherence may be due to repetition suppression caused by neural fatigue or by a more efficient encoding (Grill-Spector et al., 2006; Summerfield et al., 2008) decreases the visual persistence of the dots. Thus, fewer dots are perceived on screen simultaneously.

Finally, these examples show a novel visual method to rapidly and non-invasively appraise repetition suppression in human subjects. Deficits in repetition suppression in schizophrenia are evidenced by an impaired pre-pulse inhibition of the startle response (Hong et al., 2007; Swerdlow et al., 2006), impaired mismatch negativity (Javitt et al., 1998; Light and Braff, 2005), and abnormal processing of oddball stimuli (Kiehl and Liddle, 2001). Schizophrenic patients have a lowered CFFT (Black et al., 1975; Saucer and Sweetbaum, 1958), and generally a lower sensitivity for detecting flicker (Slaghuis and Bishop, 2001), presumably because of a non-diminishing visual persistence. Collectively, these findings paint a picture of reduced or absent repetition suppression in schizophrenic patients, presumably resulting from a deficit in cortical inhibition (Daskalakis et al., 2002). Roughly speaking, to a schizophrenic brain, certain types of repeated stimuli will continue to appear novel (Guillem et al., 2001). Consistent with these observations, results indicate that schizophrenic patients fail to perceive a differential numerosity for repeated and random stimuli.

Example 4

Testing the Proliferation Effect on Schizophrenic Patients 33 chronic schizophrenic participants were studied during their inpatient stay at Harris County Psychiatric Center. A healthy control population was also studied (n=12) that was demographically-balanced to patients with respect to age, race, years of education, and score on the Wide Range Achievement Test (WRAT), a reading test which is often used in this patient population to estimate premorbid intellect.

Participants with normal or corrected-to-normal vision sat 59 cm from a computer monitor and fixated a cross at the center of the screen. On each trial, stimuli were flashed one at a time in a randomized location within 6.6° of fixation. Participants were exposed to four blocks of 30 trials each. A block consisted of one of the following categories of stimuli: color pictures of everyday objects, 3-letter words, 3-letter nonwords, and single letters. All letter or word stimuli were white. Block conditions were randomly interleaved within each subject. Each block of trials took about 2-3 minutes to complete.

In the 30 randomly-interleaved trials within each block, stimulus durations were 10, 20 or 30 ms (fixed within a trial), and the inter-stimulus interval was always equal to the stimulus duration; this yielded presentation frequency rates of 50, 25 and 17 Hz. To ensure that stimuli were not presented in close proximity on successive frames, each stimulus was presented in a different quadrant from the previous presentation. Perceptually, this rapidly presented stimulus does not map onto the physical reality because of visual persistence.

Two conditions were employed as detailed in Example 1: in the first, the same stimulus within a category was presented (repeat condition); in the second, different stimuli were presented (random condition). Trials lasted 1320 milliseconds and ended with a mask of white noise. Participants then used a numberpad to report the number of stimuli subjectively present on screen at any one moment of time, that is, how many stimuli appeared to share screen time. This measure is their numerosity. Perceived numerosity was collected for each trial and averaged within each block and condition for each subject; this produced their "repeat" numerosity and "random" numerosity.

To examine the difference between schizophrenic and healthy subjects in repeat and random numerosity, an ANOVA was performed across groups within each block and each condition. Compared to healthy controls, schizophrenic subjects showed significantly increased numerosity in the repeat condition within all blocks (ANOVA, one-tailed t-test, p<0.05), except for Letters, which showed trend-level increased numerosity (p<0.1; see FIG. 5). There was no main effect of group on random numerosity in any block of trials except Non-words, which demonstrated that schizophrenic subject showed a trend-level increase in repeat numerosity compared to healthy controls (ANOVA, one-tailed t-test, p<0.1).

To summarize, schizophrenic subjects showed similar visual persistence for randomly presented novel stimuli compared to healthy controls, but unlike healthy controls, schizophrenic patients tend to perceive repeated stimuli as though they are novel.

All patents and publications cited herein are hereby incorporated by reference in their entirety herein. Full citations for the references cited herein are provided in the following list.

PUBLICATIONS

Appelbaum, PS, Robbins, PC, Roth, LH. Dimensionalapproach to delusions: comparison across types and diagnoses. Am J Psychiatry 1999; 156:1938.

Andreasen, N C. Negative symptoms in schizophrenia. Definition and reliability. Arch Gen Psychiatry 1982; 39:784.

Black, S., Franklin, L. M., de Silva, F. P., & Wijewickrama, H. S. (1975). The flicker-fusion threshold in schizophrenia and depression. *The New Zealand Medical Journal*, 81(535), 244-246.

Bowen, R. W., Pola, J., & Matin, L. (1974). Visual Persistence: Effects of Flash Luminance, Duration and Energy. *Vision Research*, 14, 295-303.

Braff D L, Heaton R, Kuck J, Cullum M, Moranville J, Grant I et al. The generalized pattern of neuropsychological deficits in outpatients with chronic schizophrenia with heterogeneous Wisconsin Card Sorting Test results. Arch Gen Psychiatry 1991; 48: 891-898.

Buckner, R. L., Goodman, J., Burock, M., Rotte, M., Koustaal, W., Schacter, D., et al. (1998). Functional-Anatomic Correlates of Object Priming in Humans Revealed by Rapid Presentation Event-Related fMRI. *Neuron*, 20(1 Pt 1), 285-296.

Burt, P., & Sperling, G. (1981). Time, distance, and feature trade-offs in visual apparent motion. *Psychol Rev*, 88(2), 171-195.

Daskalakis, Z. J., Christensen, B. K., Chen, R., Fitzgerald, P. B., Zipursky, R. B., & Kapur, S. (2002). Evidence for impaired cortical inhibition in schizophrenia using transcranial magnetic stimulation. *Arch Gen Psychiatry*, 59(4), 347-354.

G. Dawson, S. J. Webb, J. McPartland, *Dev Neuropsychol* 27, 403 (2005).

Diagnostic and Statistical Manual of Mental Disorder, 4th ed. American Psychiatric Association, Washington, D.C. 1994.

Z. J. Daskalakis, B. K. Christensen, P. B. Fitzgerald, R. Chen, *J Neuropsychiatry Clin Neurosci* 14, 406 (Fall, 2002).

Edwards, J, Jackson, HJ, Pattison, PE. Emotion recognition via facial expression and affective prosody in schizophrenia: a methodological review. Clin Psychol Rev 2002; 22:789.

Di Lollo, V. (1977). Temporal Characteristics of Iconic Memory. *Nature*, 267.

Eagleman, D. M. (2008). Human time perception and its illusions. *Current Opinion in Neurobiology, In press.*

Eagleman, D. M., Tse, P. U., Buonomano, D., Janssen, P., Nobre, A. C., & Holcombe, A. O. (2005). Time and the brain: how subjective time relates to neural time. *J Neurosci*, 25(45), 10369-10371.

Efron, R. (1970). The minimum duration of a perception. *Neurophysiologia*, 8, 57-63.

Fahy, F. L., Riches, I. P., & Brown, M. W. (1993). Neuronal activity related to visual recognition memory: long-term memory and the encoding of recency and familiarity information in the primate anterior and medial inferior temporal and rhinal cortex. *Exp Brain Res*, 96, 457-472.

Gandhi, S. K., Pariyadath, V., Wassef, A. A., & Eagleman, D. M. (2007). *Timing judgments in schizophrenia*. Paper presented at the Society for Neuroscience.

Grill-Spector, K., Henson, R., & Martin, A. (2006). Repetition and the brain: neural models of stimulus-specific effects. *Trends in Cognitive Sciences*, 10(1), 14-23.

Gold J, Goldberg T, Weinberger D. Prefrontal function and schizophrenic symptoms. Neuropsychiat Neuropsychol Behav Neurol 1992; 5: 253-261.

Goldberg T E, Ragland J D, Torrey E F, Gold J M, Bigelow L B, Weinberger D R. Neuropsychological assessment of monozygotic twins discordant for schizophrenia. Arch Gen Psychiatry 1990; 47: 1066-1072.

Guillem, F., Bicu, M., Hooper, R., Bloom, D., Wolf, M. A., Messier, J., et al. (2001). Memory impairment in schizophrenia: a study using event-related potentials in implicit and explicit tasks. *Psychiatry Res*, 104(2), 157-173.

Gur R C, Saykin A J, Gur R E. Neuropsychological study of schizophrenia. Schizophr Res 1991; 1: 153-162.

Gruzelier J, Seymour K, Wilson L, Jolley A, Hirsch S. Impairments on neuropsychologic tests of temporohippocampal and frontohippocampal functions and word fluency in remitting schizophrenia and affective disorders. Arch Gen Psychiatry 1988; 45: 623-629.

Henson, R., & Rugg, M. (2001). Effects of Stimulus Repetition on Latency of the BOLD Impulse Response. *NeuroImage*, 13, 683.

Herrick, R. M. (1974). Frequency thresholds for two-flash flicker and critical flicker: why they differ. *Perception and Psychophysics*.

Hong, L. E., Summerfelt, A., Wonodi, I., Adami, H., Buchanan, R. W., & Thaker, G. K. (2007). Independent Domains of Inhibitory Gating in Schizophrenia and the Effect of Stimulus Interval. *Am J. Psychiatry.*, 164, 61-65.

Ishai, A., Bikle, P. C., & Ungerleider, L. G. (2006). Temporal dynamics of face repetition suppression. *Brain Research Bulletin*, 70, 289-295.

Javitt, D. C., Grochowski, S., Shelley, A., & Ritter, W. (1998). Impaired mismatch negativity (MMN) gneration in schizophrenia as a function of stimulus deviance, probability, and interstimulus/interdeviant interval. *Electroencephalography and clinical Neurophysiology*, 108, 143-153.

Kanai, R., Paffen, C. L., Hogendoorn, H., & Verstraten, F. A. (2006). Time dilation in dynamic visual display. *J Vis*, 6(12), 1421-1430.

Kanai, R., & Watanabe, M. (2006). Visual onset expands subjective time. *Percept Psychophys*, 68(7), 1113-1123.

Kiehl, K. A., & Liddle, P. F. (2001). An event-related functional magnetic resonance imaging study of an auditory oddball task in schizophrenia. *Schizophrenia Research*, 48, 159-171.

Kolers, P., & von Grunau, M. (1976). Shape and color in apparent motion. *Vision Research*, 16, 329-335.

Liddle P F, Morris D L. Schizophrenic syndromes and frontal lobe performance. Br J Psychiatry 1991; 158: 340-345.

Light, G. A., & Braff, D. L. (2005). Mismatch negativity deficits are associated with poor functioning in schizophrenia patients. *Arch Gen Psychiatry*, 62, 127-136.

Miller, E. K., & Desimone, R. (1994). Parallel neuronal mechanisms for short-term memory. *Science*, 263(5146), 520-522.

Moore, C. M., Mordkoff, J. T., & Enns, J. T. (2007). The path of least persistence: object status mediates visual updating. *Vision Res*, 47(12), 1624-1630.

Morrone, M. C., Ross, J., & Burr, D. (2005). Saccadic eye movements cause compression of time as well as space. *Nat Neurosci*, 8(7), 950-954.

Nakajima, Y., ten Hoopen, G., Hilkhuysen, G., & Sasaki, T. (1992). Time-shrinking: a discontinuity in the perception of auditory temporal patterns. *Percept Psychophys*, 51(5), 504-507.

Navon, D. (1976). Irrelevance of figural identity for resolving ambiguities in apparent motion. *J Exp Psychol Hum Percept Perform*, 2(1), 130-138.

Pariyadath, V., & Eagleman, D. M. (2007). The effect of predictability on subjective duration. *PLoS ONE*, 2(11), 1264.

G. Rainer, E. K. Miller, Neuron 27, 179 (2000).

Rose, D., & Summers, J. (1995). Duration illusions in a train of visual stimuli. *Perception*, 24(10), 1177-1187.

Russell, A J, Munro, J C, Jones, P B, et al. Schizophrenia and the myth of intellectual decline. Am J Psychiatry 1997; 154:635.

Saykin, A J, Gur, R C, Gur, R E, et al. Neuropsychological function in schizophrenia. Selective impairment in memory and learning. Arch Gen Psychiatry 1991; 48:618.

Saucer, R. T., & Sweetbaum, H. (1958). Perception of the shortest noticeable dark time by schizophrenics. *Science*, 127(3300), 698-699.

Seidman, L J, Buka, S L, Goldstein, J M, Tsuang, M T. Intellectual decline in schizophrenia: evidence from a prospective birth cohort 28 year follow-up study. J Clin Exp Neuropsychol 2006; 28:225.

Slaghuis, W. L., & Bishop, A. M. (2001). Luminance flicker sensitivity in positive- and negative-symptom schizophrenia. *Exp Brain Res*, 138, 88-99.

Summerfield, C., Trittschuh, E. H., Monti, J. M., Mesulam, M. M., & Egner, T. (2008). Neural repetition suppression reflects fulfilled perceptual expectations. *Nat Neurosci.*

Swerdlow, N. R., Light, G. A., Cadenhead, K. S., Sprock, J., Hsieh, M. H., & Braff, D. L. (2006). Startle gating deficits in a large cohort of patients with schizophrenia: relationship to medications, symptoms, neurocognition, and level of function. *Arch Gen Psychiatry*, 63(12), 1325-1335.

Szymanski, S R, Cannon, T D, Gallacher, F, et al. Course of treatment response in first-episode and chronic schizophrenia. Am J Psychiatry 1996; 153:519.

C. M. Thiel, R. N. A. Henson, J. S. Morris, K. J. Friston, R. J. Dolan, *J Neurosci* 21, 6846 (2001).

Tse, P. U., Intriligator, J., Rivest, J., & Cavanagh, P. (2004). Attention and the subjective expansion of time. *Perception & Psychophysics*, 66(7), 1171-1189.

Ulrich, R., Nitschke, J., & Rammsayer, T. (2006). Perceived duration of expected and unexpected stimuli. *Psychological Research*, 70, 77-87.

Woodberry, K A, Giuliano, A J, Seidman, L J. Premorbid I Q in schizophrenia: a meta-analytic review. Am J Psychiatry 2008; 165:579.

Yarrow, K., Haggard, P., Heal, R., Brown, P., & Rothwell, J. C. (2001). Illusory perceptions of space and time preserve cross-saccadic perceptual continuity. *Nature*, 414(6861), 302-305.

What is claimed is:

1. A device for assessing visual persistence in an individual, comprising:

a computing display configured to display a sequence of stimulus, wherein each stimulus is configured to be displayed for a time period less than a predetermined perception limit and wherein at least one of the sequence of stimulus is configured to be displayed in a location different from the previously displayed stimulus;

and a user input configured to receive an input from a user corresponding to the number of displayed stimuli simultaneously perceived by the individual.

2. The device of claim 1, wherein each stimulus is the same.

3. The device of claim 1, wherein the device is further configured to assess a cognitive disorder by comparing the number of perceived stimuli with a predetermined number.

4. The device of claim 3, wherein the cognitive disorder is schizophrenia, autism, drug use, or traumatic brain injury.

5. The device of claim 1, wherein the predetermined perception limit is between 70 and 110 ms.

* * * * *